(12) United States Patent
Shi

(10) Patent No.: US 10,524,708 B2
(45) Date of Patent: Jan. 7, 2020

(54) SAFE AND CONVENIENT DISPOSABLE BLOOD-TAKING NEEDLE WITH DOUBLE-SURFACE CAP

(71) Applicant: STERILANCE MEDICAL (SUZHOU) INC., Suzhou, Jiangsu (CN)

(72) Inventor: Guoping Shi, Suzhou (CN)

(73) Assignee: STERILANCE MEDICAL (SUZHOU) INC., Suzhou (CN)

( * ) Notice: Subject to any disclaimer, the term of this patent is extended or adjusted under 35 U.S.C. 154(b) by 0 days.

(21) Appl. No.: 14/758,316

(22) PCT Filed: Oct. 31, 2013

(86) PCT No.: PCT/CN2013/086333
§ 371 (c)(1),
(2) Date: Jun. 29, 2015

(87) PCT Pub. No.: WO2014/101569
PCT Pub. Date: Jul. 3, 2014

(65) Prior Publication Data
US 2015/0351677 A1    Dec. 10, 2015

(30) Foreign Application Priority Data

Dec. 28, 2012    (CN) .......................... 2012 1 0586058

(51) Int. Cl.
*A61B 5/15*        (2006.01)
*A61B 5/151*       (2006.01)

(52) U.S. Cl.
CPC .... *A61B 5/15105* (2013.01); *A61B 5/150022* (2013.01); *A61B 5/15142* (2013.01);
(Continued)

(58) Field of Classification Search
None
See application file for complete search history.

(56) References Cited

U.S. PATENT DOCUMENTS 5,385,571 A * 1/1995 Morita ............... A61B 5/15142
606/181
2003/0073933 A1 * 4/2003 Hirao ............... A61B 5/150022
600/576

(Continued)

FOREIGN PATENT DOCUMENTS

CN    2482968 Y    3/2002
CN    2902192 Y    5/2007
(Continued)

OTHER PUBLICATIONS

Jan. 30, 2014 International Search Report issued in International Patent Application No. PCT/CN2013/086333.

*Primary Examiner* — Sean P Dougherty
*Assistant Examiner* — Benjamin S Melhus
(74) *Attorney, Agent, or Firm* — Oliff PLC

(57) ABSTRACT

A disposable blood-taking needle with double-surface cap includes a lancet body with a needle tip, a lancet handle and a lancet cap. The lancet body is fixed inside the lancet handle and the needle tip extends out of the first end of the lancet handle to be inserted into the lancet cap. The body of the lancet cap is a block structure, which includes a first face and a second face. Both the first face and second face are flat and opposed such that when one face faces upwards, the other face faces downwards and the included angle between them in space is less than 45°; the first face is provided with a first blind hole and the second face is provided with a second blind hole and both the first blind hole and the second blind hole match the first end of the lancet handle in respect of connection relationship. In the block structure, except the first face and the second face, the other external surfaces are arcuate faces protruding outward and/or angular faces protruding outward.

5 Claims, 7 Drawing Sheets

(52) U.S. Cl.
CPC .. *A61B 5/150435* (2013.01); *A61B 5/150503* (2013.01); *A61B 5/150549* (2013.01); *A61B 5/150618* (2013.01); *A61B 5/150717* (2013.01)

(56) References Cited

U.S. PATENT DOCUMENTS

| | | | |
|---|---|---|---|
| 2005/0131441 A1* | 6/2005 | Iio | A61B 5/15186 606/182 |
| 2007/0293883 A1 | 12/2007 | Horie | |
| 2010/0121368 A1 | 5/2010 | Kim | |

FOREIGN PATENT DOCUMENTS

| | | |
|---|---|---|
| CN | 101778599 A | 7/2010 |
| CN | 103006240 A | 4/2013 |
| CN | 203074711 U | 7/2013 |

* cited by examiner

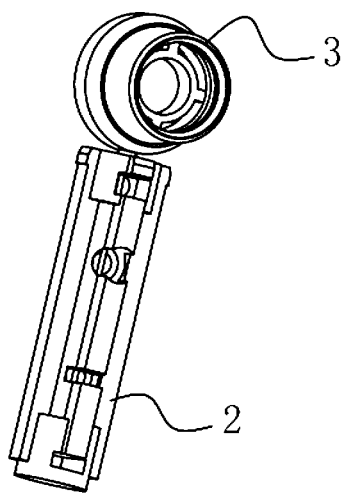
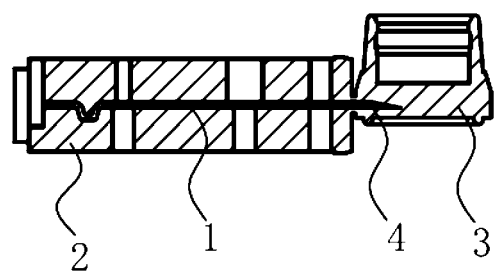
FIG. 1
PRIOR ART
FIG. 2
PRIOR ART
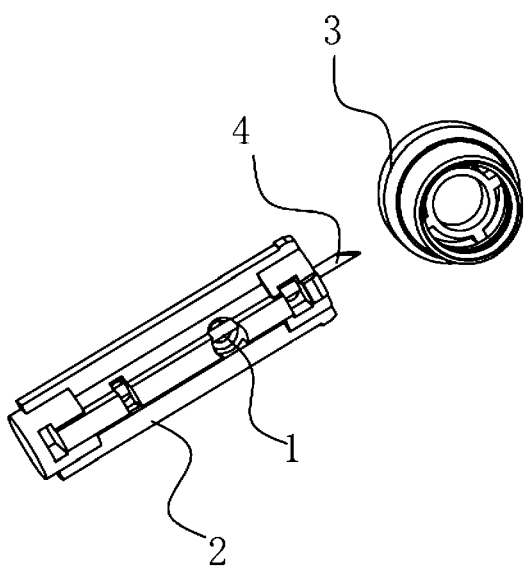
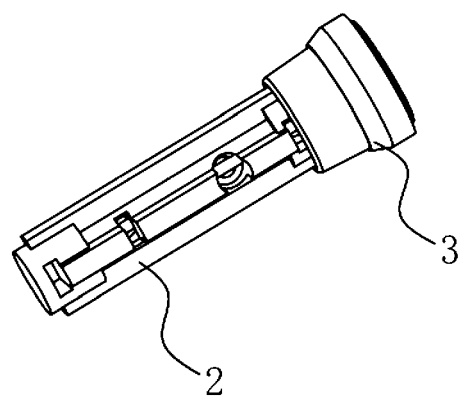
FIG. 3
PRIOR ART
FIG. 4
PRIOR ART

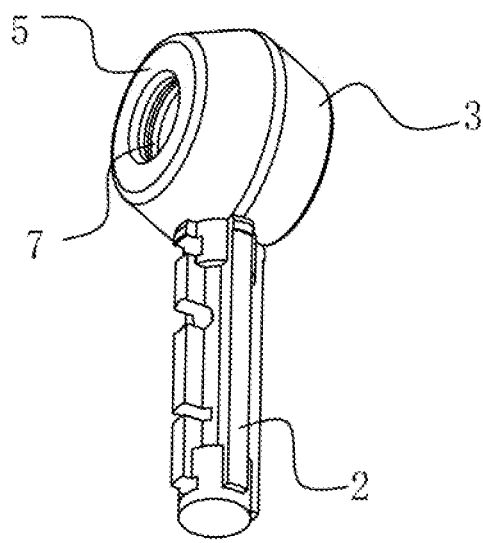
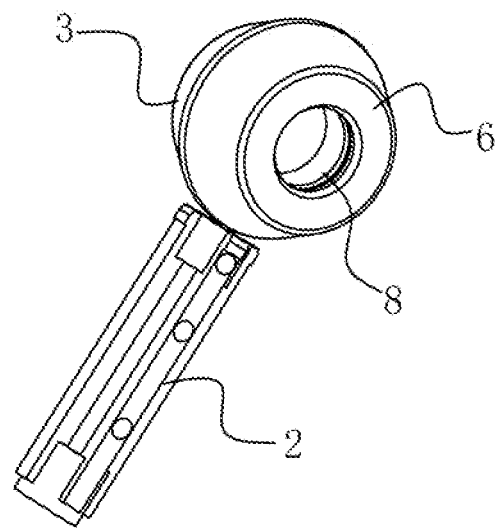
FIG. 5  FIG. 6
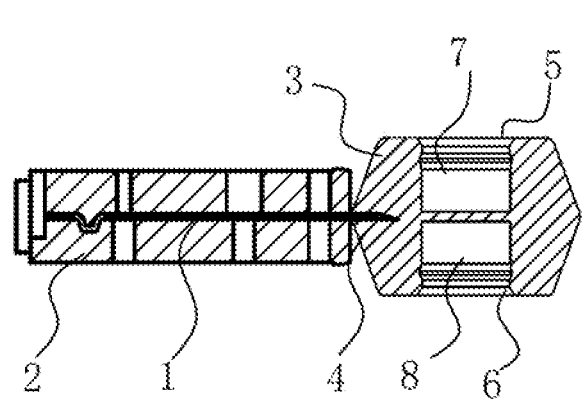
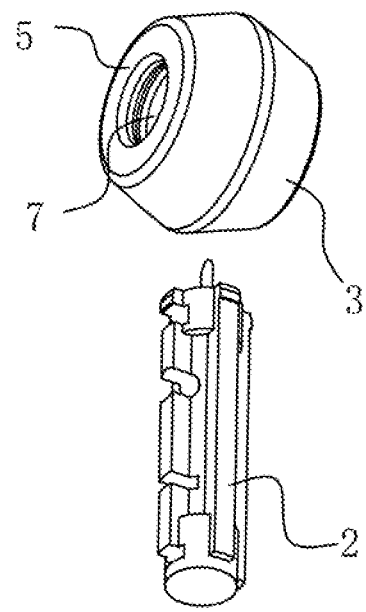
FIG. 7  FIG. 8

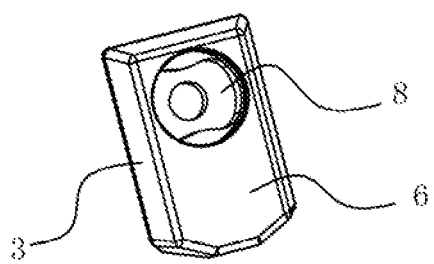
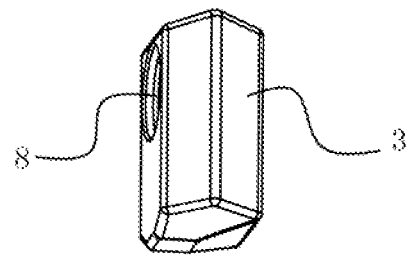
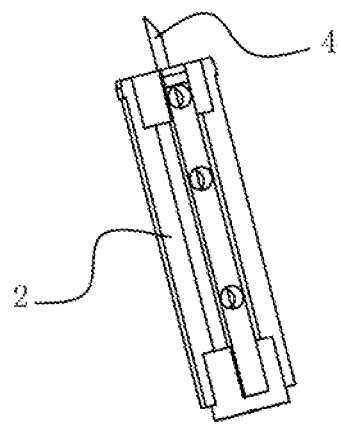
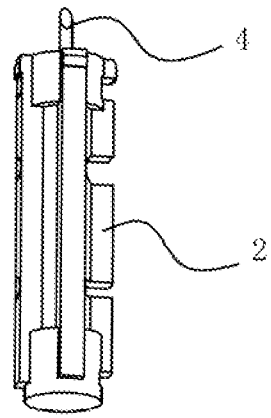
FIG. 18
FIG. 19
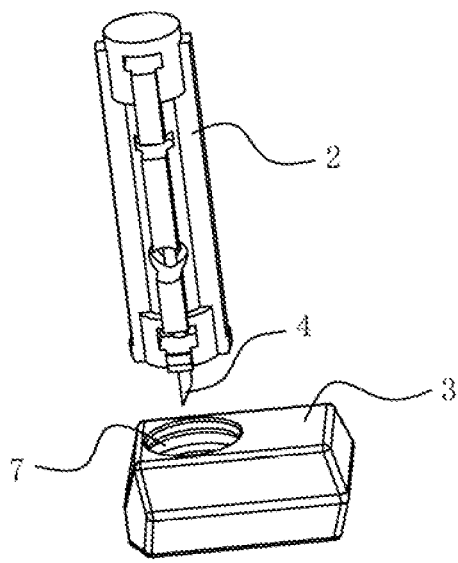
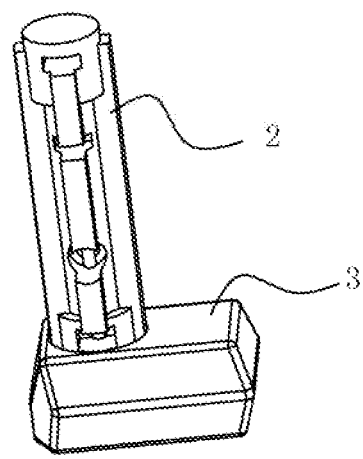
FIG. 20
FIG. 21

SAFE AND CONVENIENT DISPOSABLE BLOOD-TAKING NEEDLE WITH DOUBLE-SURFACE CAP

TECHNICAL FIELD

The present invention relates to a kind of medical disposable lancet, particularly to a kind of safe and convenient disposable blood-taking needle with double-surface cap. This lancet improves the design of lancet cap on the basis of previous safe and convenient design; therefore its application becomes safer and more convenient to be especially suitable for domestic care and blood sampling.

BACKGROUND OF INVENTION

As blood glucose testing technology has improved, the volume of blood sampling volume required by the measuring instruments has become less and less. In order to reduce the pain for patients, the diameter of the sampling needle has become thinner. The diameter of current needles vary from 21 G (Φ0.8 mm), 23 G (Φ0.64 mm), 26 G (Φ0.46 mm), 28 G (Φ0.36 mm), 30 G (Φ0.30 mm), 32 G (Φ0.25 mm) to 33 G (Φ0.20 mm). Chinese patent CN2482968Y discloses a kind of utility model patent named *Disposable Injection Lancet*. The lancet of the patent consists of a lancet body with needle tip, lancet handle and lancet cap. The lancet body is fixed inside the lancet handle, the needle tip extends out of the end of lancet handle to be inserted into the lancet cap when the lancet handle and lancet cap are connected by the transition structure enveloping the lancet body. The lancet body of the lancet is made from stainless steel, and the lancet handle and lancet cap are made from plastics. During device production, the lancet body is placed inside a die cavity for one-shot injection moulding to permanently fix the lancet body inside the lancet handle and lancet cap made from plastics. During use, the cap is twisted to break the transition connection of lancet handle and lancet cap, and is then removed to expose the needle tip of certain length. The lancet handle is installed in the lancing device for blood sampling. In a clinical setting, this kind of lancet is usually disposed of directly in a sharps bin after use to prevent cross infection or needle stick without inserting the needle tip into the lancet cap or otherwise protecting the exposed needle. However, in a domestic setting where dedicated sharps disposal may be absent, the lancet cap must be retained so that the needle tip can be inserted into the needle cap by piercing to provide discrete protection against contamination and needle stick injury. At a diameter of less than 30 G (Φ0.30 mm), the lancet body and needle tip may be weak and easily bent and piercing of the needle tip into the lancet cap to affect protection may be difficult, causing the the needle tip to remain exposed.

In order to solve the above-mentioned problem, another kind of lancet is available in prior art, i.e. a capping lancet. Refer to FIG. 1 through 4. This is another kind of technical solution for protecting the needle tip with the lancet cap after use. This kind of lancet consists of lancet body 1 with needle tip 4, lancet handle 2 and lancet cap 3. The lancet cap 3 has the a concave shape with one blind hole. One end of blind hole is the open end of lancet cap 3 and the other end of blind hole is base end of lancet cap 3. Before use, needle tip 4 is inserted in the base end of lancet cap 3 (see FIG. 2) and after use, needle tip 4 is inserted into the blind hole from the insertion end (see FIG. 4). When the diameter of lancet body 1 is very thin, the application of this form of cap avoids the impracticable piercing of the needle tip 4 into lancet cap 3 or needle tip bending. Two methods are available for use of this form of lancet capping: one method is to place the separated lancet cap 3 on a work table, whereby the orientation of the open end of the lancet cap must be manually adjusted so it is presented correctly for capping. This method is relatively safe, but adds the supporting action of correctly orienting the lancet cap 3 manually, reducing simplicity and speed. The other capping method is that the user holds the lancet handle 2 with one hand and picks up the lancet cap 3 with the other hand to manually orient it and insert needle tip 4. This kind of operation is simple and convenient, but lacks needle stick safety, especially for elderly patients or patients with poor eyesight or dexterity. Therefore, the object of present invention is to design one type of safe, convenient and user friendly disposable lancet which addresses these problems.

Disclosure of the Invention

The present invention provides a type of safe and convenient disposable blood-taking needle with double-surface cap. It has been devised to address the problem of safety and convenience of capping after use of a disposable lancet.

In order to achieve the above object, the present invention provides the technical solution: a kind of safe and convenient disposable blood-taking needle with double-surface cap, comprising a lancet body with needle tip, lancet handle and lancet cap. The lancet body is fixed inside the lancet handle and the needle tip extends out of the first end of lancet handle to be inserted into the lancet cap.

The body of above described lancet cap is a block structure, which is provided with a first face and second face. Both first face and second face are flat and opposed, such that when one face faces upwards, the other face faces downwards and the included angle between them in space is less than 45°; the first face is provided with first blind hole and second face is provided with second blind hole and both first blind hole and second blind hole match the first end of lancet handle in respect of connection relationship;

In the above described block structure, except the first face and second face, the other external surfaces are arcuate faces protruding outward and/or angular faces protruding outward.

The above described technical solution is explained as follows:

1. In the above described technical solution, the block structure means the spatial structure with a block-like shape.

2. In the above described technical solution, "upwards" and "downwards" includes the parallelism of two faces, and also includes the nonparallelism, i.e. the included angle between two faces in space is less than 45°.

3. In the above described technical solution, the angular face means an angular face protruding outward with respect of the lancet cap.

4. In the above described technical solution, the block structure is a flat structure and the top surface of flat structure is the first face and bottom surface of the flat structure is the second face.

5. In the above described technical solution, the first blind hole and second blind hole may be coaxially arranged in the direction of the hole axis; otherwise, the first blind hole and second blind hole could also be arranged off-axis in the direction of hole axis.

The design concept and operating principle of the present invention is: Since the two kinds of insertion methods of needle tip into lancet cap after use of existing twist cap disposable lancet previously described are complicated and not relatively safe, the overall design concept of the present invention is that: when the user places the lancet cap on a work table, the lancet cap is always in an insertion-ready state for the needle tip of the used lancet. Therefore, the open end of the lancet cap shall always face upwards when the lancet cap of a double-sided cap disposable lancet is placed in any manner on a work table. The lancet cap incorporates a stable flat surface making it possible for the user to safely insert the needle tip into the lancet cap on a work table with one hand.

The particular design concept and operating principle of present invention is: The body of the above described lancet cap is a block structure, which is provided with a first face and second face. Both first face and second face are flat. When one face faces upwards, the other face faces downwards and the included angle between them in space is less than 45°; the first face is provided with a first blind hole and second face is provided with a second blind hole and both first blind hole and second blind hole match the first end of lancet handle in respect of connection relationship, making both sides suitable for insertion of the first end of the lancet handle into the blind hole; in the above described block structure, except the first face and second face, the other external surfaces are arcuate faces protruding outward or/and angular faces protruding outward, and when the lancet cap is placed in any manner on a work table, the structure makes it impossible for the lancet cap to rest on the external surfaces, such that the lancet cap could only rest on the first face or second face thus keeping the open end of the lancet cap always facing upward. The open end of the lancet cap means the end with the blind hole on the first face or second face; furthermore, the block structure is a flat structure and the top surface of the flat structure is the first face and the bottom surface of the flat structure is the second face, which makes the height of the lancet cap lower and cross sectional area of the lancet cap larger. This structure makes it impracticable for the lancet cap to rest on the other external surfaces and assists in keeping the open end of lancet cap always facing upward. Additionally, it makes it difficult for the user to pick up the lancet cap by hand and encourages the user to insert the first end of lancet handle into the lancet cap directly on the work table with one hand, which ensures the safety of the user.

Due to application of the above described technical solution, the present invention has the following advantages and effects in comparison with existing technologies: the safe and convenient disposable blood-taking needle with double-surface cap provided by the present invention is especially suitable for domestic care, as it could improve safety by effectively preventing the risk of needle stick by a used lancet during capping and it also has the advantage of speed and convenience.

BRIEF DESCRIPTION OF THE DRAWINGS

FIG. 1 is the perspective view of a twist capping lancet of existing technology;

FIG. 2 is the cross sectional view of a twist capping lancet of existing technology;

FIG. 3 is the perspective view illustrating the state of a twist capping lancet of existing technology after removing the lancet cap;

FIG. 4 is the perspective view illustrating the state of a twist capping lancet of existing technology after inserting the used needle tip into the lancet cap;

FIG. 5 is a front perspective view of embodiment 1 of the present invention;

FIG. 6 is a back perspective view of embodiment 1 of the present invention;

FIG. 7 is an exploded perspective view of embodiment 1 of the present invention;

FIG. 8 is a perspective view illustrating the state after removing the lancet cap of embodiment 1;

FIG. 18 is a perspective view illustrating the state 2 after removing the lancet cap of embodiment 2;

FIG. 19 is a side view of FIG. 18;

FIG. 20 is a perspective view illustrating the state of inserting the used needle tip into lancet cap of embodiment 2;

FIG. 21 is a perspective view illustrating the state after inserting the used needle tip into lancet cap of embodiment 2;

In the above described figures: 1. lancet body; 2. lancet handle; 3. lancet cap; 4. needle tip; 5. first face; 6. second face; 7. first blind hole; 8. second blind hole; 9. interconnecting hole.

SPECIFIC EMBODIMENT

With reference to the accompanying drawings and embodiment, the present invention will be described in detail.

Figure 23:
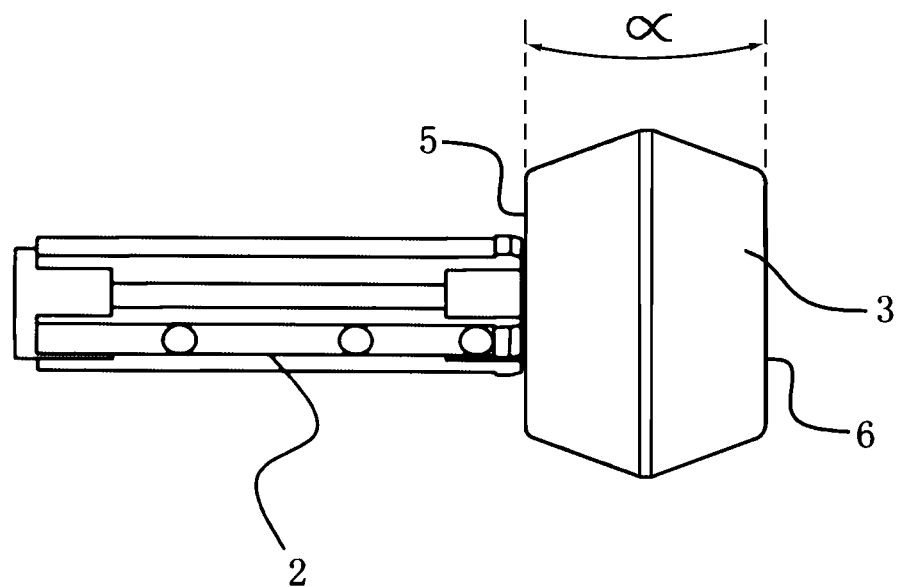
FIG. 23 shows an angle between two flat faces.

Embodiment 1: A Kind of Safe and Convenient Disposable Blood-Taking Needle with Double-Surface Cap As shown in FIG. 5 through 10, the lancet of the present invention consists of lancet body 1 with needle tip 4, lancet handle 2 and lancet cap 3. The lancet body 1 is fixed inside the lancet handle 2 and the needle tip 4 extends out of the first end of lancet handle 2 to be inserted into the lancet cap 3. The body of above described lancet cap 3 is a block structure, which is provided with first face 5 and second face 6. Both first face 5 and second face 6 are flat faces. And when one face faces upwards, the other face faces downwards and the included angle α (see, FIG. 23) between them in space is less than 45°; the first face 5 is provided with first blind hole 7 and second face 6 is provided with second blind hole 8 and both first blind hole 7 and second blind hole 8 match the first end of lancet handle 2 in respect of connection relationship. In the above described block structure, except the first face 5 and second face 6, the other external surfaces are arcuate faces protruding outward and angular faces protruding outward. The above described first blind hole 7 and second blind hole 8 are coaxially arranged in the direction of hole axis.

Embodiment 2: A Kind of Safe and Convenient Disposable Blood-Taking Needle with Double-Surface Cap As shown in FIG. 11 through 21, the lancet of the present invention consists of lancet body 1 with needle tip 4, lancet handle 2 and lancet cap 3. The lancet body 1 is fixed inside the lancet handle 2 and the needle tip 4 extends out of the first end of lancet handle 2 to be inserted into the lancet cap 3. The body of above described lancet cap 3 is a block structure, which is flat structure and the top surface of the flat structure is first face 5 and bottom surface of the flat structure is second face 6. Both first face 5 and second face 6 are flat faces. And when one face faces upwards, the other face faces downwards and the included angle between them in space is less than 45'; the first face 5 is provided with first blind hole 7 and second face 6 is provided with second blind hole 8 and both first blind hole 7 and second blind hole 8 match the first end of lancet handle 2 in respect of connection relationship. In the above described block structure, except the first face 5 and second face 6, the other external surfaces are angular faces protruding outward. The above described first blind hole 7 and second blind hole 8 are arranged off-axis in the direction of hole axis.

The particular operation process of above described two embodiments is as follows: when the blood sampling is required, remove the lancet cap 3 to expose the needle tip 4 for blood sampling, and afterward insert the first end of lancet handle 2 with needle tip 4 into lancet cap 3 to protect the sharp needle tip. As both sides of lancet cap 3 are suitable for insertion of the first end of lancet handle 2 into the blind hole, i.e. first blind hole 7 and second blind hole 8; and since, except the first face 5 and second face 6, the other external surfaces are arcuate faces protruding outward or/and angular faces protruding outward, when the lancet cap 3 is placed in any manner on a work table, the structure makes it impossible for the lancet cap 3 to rest on the other external surfaces, so the lancet cap 3 can only rest on the first face 5 or second face 6, which makes the height of the lancet cap lower and cross sectional area of the lancet cap larger. This structure makes it impracticable for the lancet cap 3 to rest on the other external surfaces and assists in keeping the open end of lancet cap 3 always facing upward. Additionally, it makes it difficult for the user to pick up the lancet cap 3 by hand and encourages the user to insert first end of lancet handle 2 into the lancet cap 3 on the work table with one hand, which ensures the safety of the user.

Figure 9:
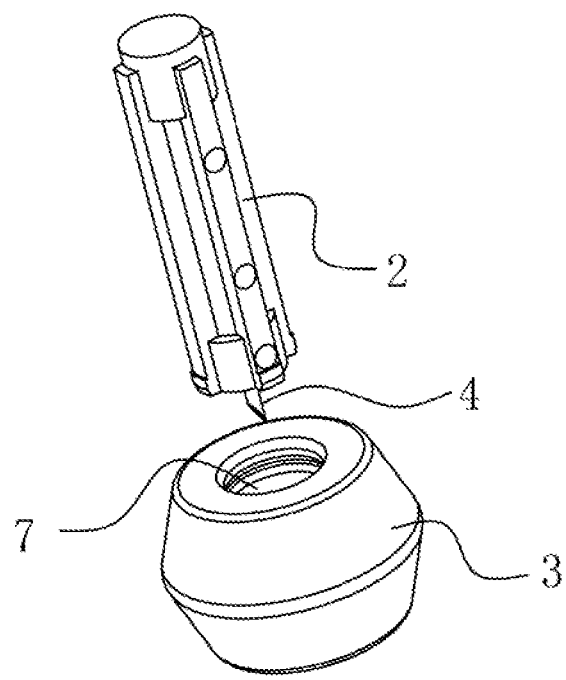
FIG. 9 is a perspective view illustrating the state of inserting the used needle tip into the lancet cap of embodiment 1.
Figure 10:
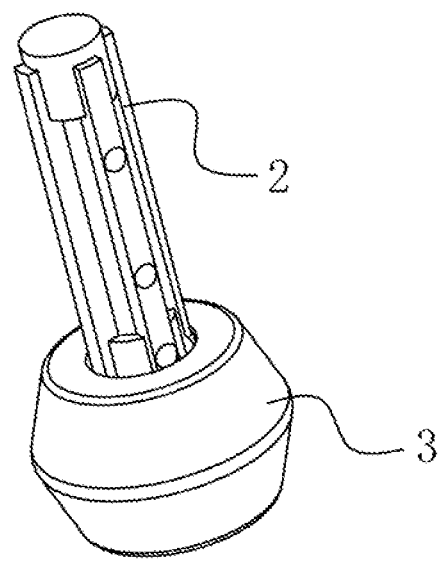
FIG. 10 is a perspective view illustrating the state of embodiment 1 after inserting the used needle tip into the lancet cap.
Figures 11, 12:
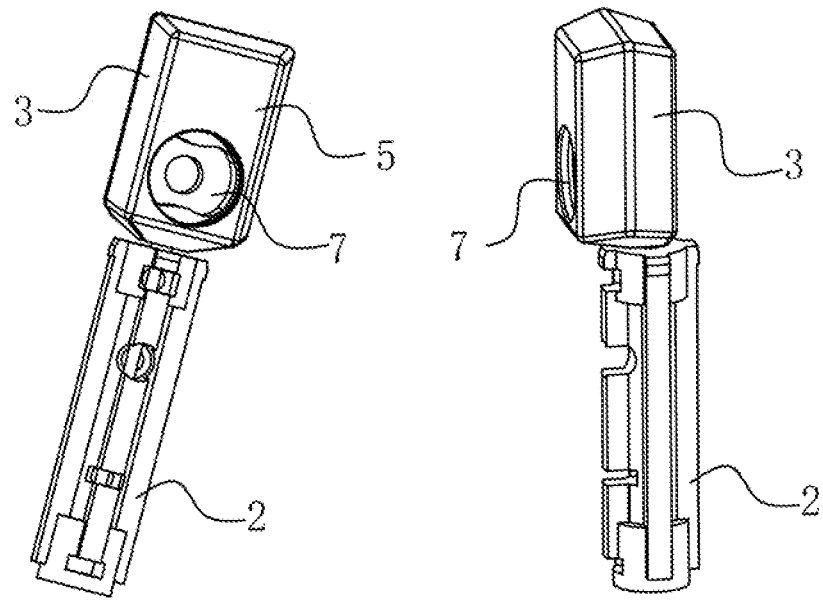
FIG. 11 is a front perspective view of embodiment 2 of the present invention.
FIG. 12 is a side view of FIG. 11.
Figures 13, 14:
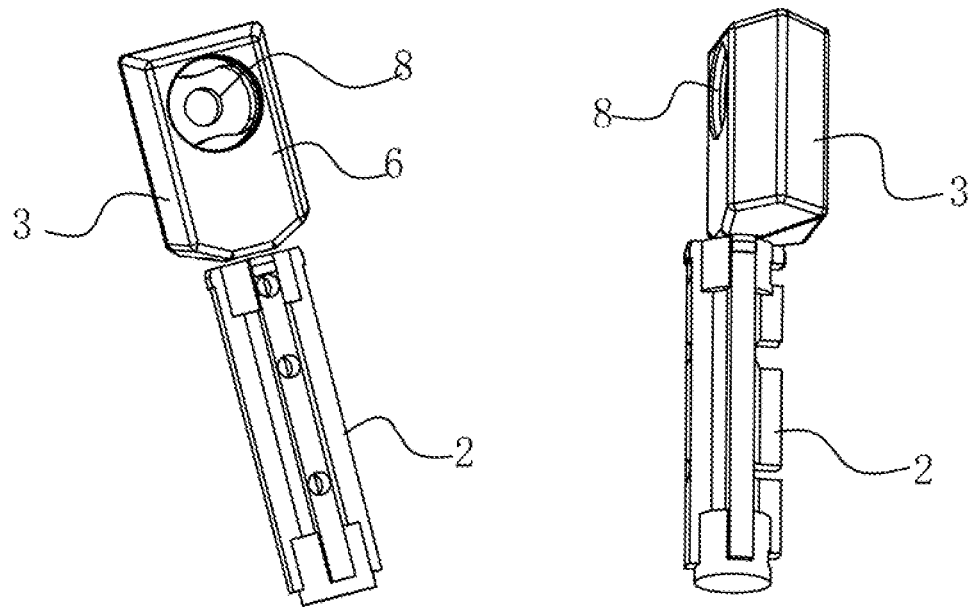
FIG. 13 is a back perspective view of embodiment 2 of the present invention.
FIG. 14 is a side view of FIG. 13.
Figure 15:
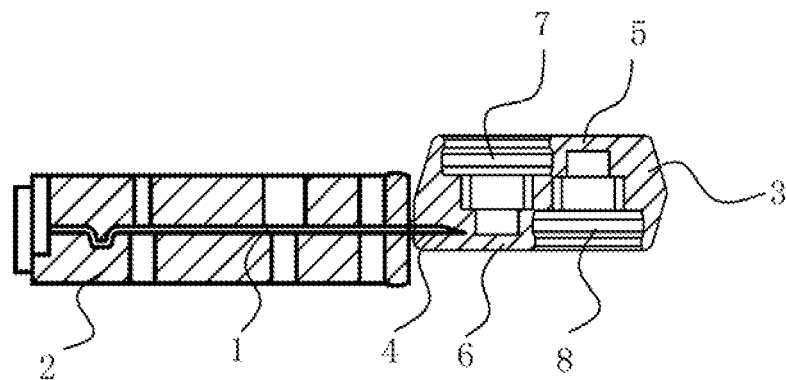
FIG. 15 is an exploded perspective view of embodiment 2 of the present invention.
Figures 16, 17:
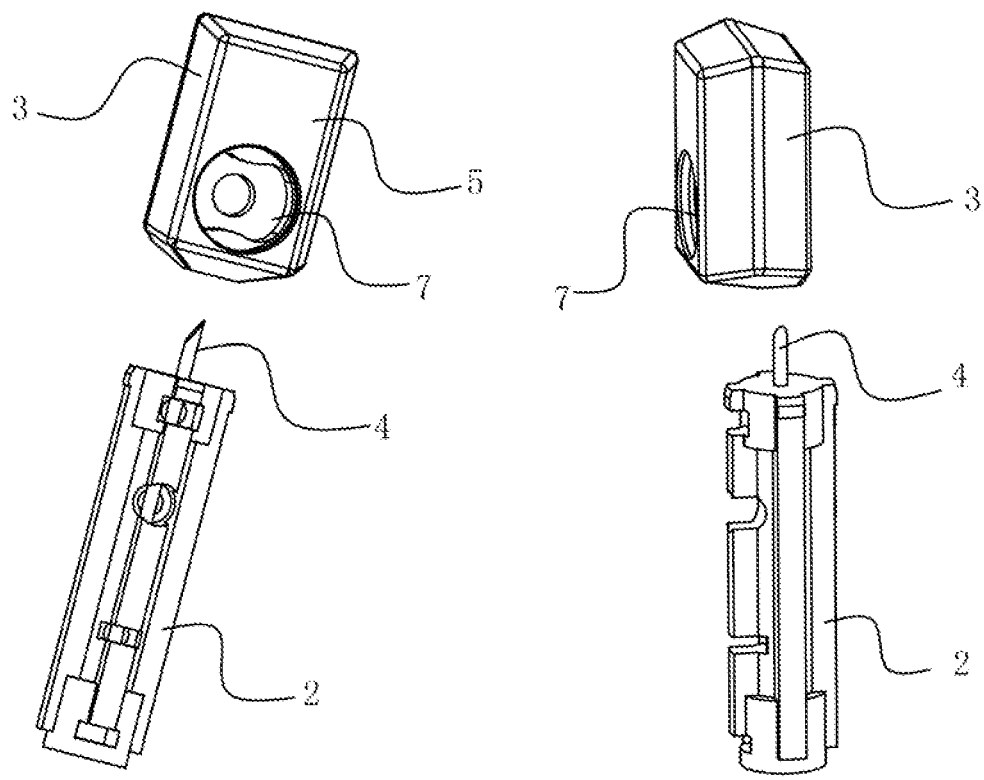
FIG. 16 is a perspective view illustrating the state 1 after removing the lancet cap of embodiment 2.
FIG. 17 is a side view of FIG. 16.
Figure 22:
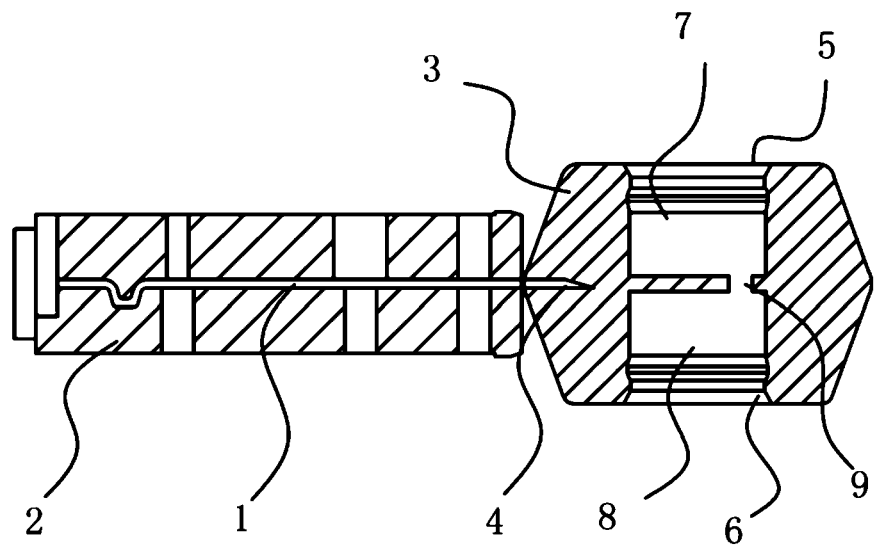
FIG. 22 is a perspective view illustrating the structure change of FIG. 7.

It should be noted that the above described embodiments are only for illustration of technical concept and characteristics of present invention with the purpose of making those skilled in the art understand the present invention, and thus these embodiments shall not limit the protection range of present invention. The equivalent changes or modifications according to spiritual essence of present invention shall fall in the protection scope of present invention. Take embodiment 1 for example, refer to FIG. 22 for equivalent change on the basis of above described embodiment 1. There is an interconnecting hole 9 between first blind hole 7 and second blind hole 8. The interconnecting hole 9 is a small hole, which doesn't affect the essence of first blind hole 7 and second blind hole 8 being blind holes and doesn't affect the technical concept and effect realization of the present invention.

The invention claimed is:

1. A disposable lancet having a blood-taking needle, the disposable lancet comprising:
   a lancet body with a needle tip;
   a lancet handle having a first end; and
   a lancet cap, the lancet body being fixed inside the lancet handle and the needle tip extending out of the first end of the lancet handle to be inserted into the lancet cap, wherein:
   the lancet cap is a block structure having a height, a length and a width, the block structure has a first face and a second face, and the first face and the second face are flat and have a distance therebetween and an included angle therebetween, the distance between the first face and the second face defining the height of the block structure;
   when one of the first face and the second face faces upwards, the other of the first face and the second face faces downwards;
   the included angle between the first face and the second face is less than 45°;
   the first face is provided with a first blind hole and the second face is provided with a second blind hole and both the first blind hole and the second blind hole match the first end of the lancet handle in respect of a connection relationship;
   the first blind hole and the second blind hole have a central axis in the hole depth direction, and are coaxially arranged along the central axis in the hole depth direction, the first blind hole and the second blind hole are separated by a distance between each other in the hole depth direction;
   within the distance between the first blind hole and the second blind hole, both an interconnecting hole and a portion of the lancet cap are provided between the first blind hole and the second blind hole, and the interconnecting hole connects the first blind hole to the second blind hole;
   the height of the block structure is smaller than the length of the block structure and is smaller than the width of the block structure, and all external surfaces of the block structure, except the first face and the second face, are at least one of: (i) arcuate faces protruding outward, or (ii) angular faces protruding outward;
   as a result of the arcuate faces or angular faces protruding outward, when the lancet cap is detached from the lancet body and the lancet handle, and when any of the external surfaces of the lancet cap is placed on a flat surface, the lancet cap is configured to: (i) stably rest on the first face when the first face faces down to stably rest on the flat surface, and (ii) stably rest on the second face when the second face faces down to stably rest on the flat surface, and thereby preventing the lancet cap from stably resting on any of the external faces other than the first face and the second face;
   as a result of the arcuate faces or angular faces protruding outward, the one of the first face or the second face faces down to stably rest on the flat surface and the other of the first face and the second face faces up; and
   as a result of the arcuate faces or angular faces protruding outward, the first blind hole faces up and is in an insertion-ready state for the first end of the lancet handle to insert into to hide the needle tip when the second face faces down to stably rest on the flat surface, and the second blind hole faces up and is in an insertion-ready state for the first end of the lancet handle to insert into to hide the needle tip when the first face faces down to stably rest on the flat surface.

2. The disposable lancet according to claim 1, wherein the block structure is a flat structure having a top surface and a bottom surface, and the top surface of the flat structure is the first face and the bottom surface of the flat structure is the second face.

3. The disposable lancet according to claim 1, wherein the interconnecting hole is smaller than each of the first blind hole and the second blind hole.

4. A disposable lancet having a blood-taking needle, the disposable lancet comprising:
   a lancet body with a needle tip;
   a lancet handle having a first end; and
   a lancet cap comprising:
      a first face, a second face, and a third face;
      a first hole on the first face, the first hole being a first blind hole;
      a second hole on the second face, the second hole being a second blind hole; and
      a third hole on the third surface, the lancet body being fixed inside the lancet handle and the needle tip extending out of the first end of the lancet handle to be inserted into the first blind hole, the second blind hole, or the third hole of the lancet cap, wherein:
   the lancet cap is a block structure having a height, a length and a width, the block structure includes the first face, the second face, and the third face, and the first face and the second face are flat and have a distance therebetween and an included angle therebetween, the distance between the first face and the second face defining the height of the block structure;
   when one of the first face and the second face faces upwards, the other of the first face and the second face faces downwards, and the third face faces in a sideways direction that is neither upwards or downwards;
   the included angle between the first face and the second face is less than 45°;
   the first blind hole has a first central axis in a hole depth direction into the first face, the second blind hole has a second central axis in a hole depth direction into the second face, the third hole has a third central axis in a hole depth direction into the third face, the third central axis being perpendicular to both the first central axis and the second central axis;
   the first central axis and second central axis are parallel in the hole depth direction, the first central axis and second central axis are separated by a distance from each other in a direction perpendicular to the hole depth direction;
   the height of the block structure is smaller than the length of the block structure and is smaller than the width of the block structure, and all external surfaces of the block structure, except the first face and the second face, are at least one of: (i) arcuate faces protruding outward, or (ii) angular faces protruding outward;
   as a result of the arcuate faces or angular faces protruding outward, when the lancet cap is detached from the lancet body and the lancet handle, and when any of the external surfaces of the lancet cap is placed on a flat surface, the lancet cap is configured to: (i) stably rest on the first face when the first face faces down to stably rest on the flat surface, and (ii) stably rest on the second face when the second face faces down to stably rest on the flat surface, and thereby preventing the lancet cap from stably resting on any of the external faces other than the first face and the second face;
   as a result of the arcuate faces or angular faces protruding outward, the one of the first face or the second face faces down to stably rest on the flat surface and the other of the first face and the second face faces up; and
   as a result of the arcuate faces or angular faces protruding outward, the first blind hole faces up and is in an insertion-ready state for the first end of the lancet handle to insert into to hide the needle tip when the second face faces down to stably rest on the flat surface, and the second blind hole faces up and is in an insertion-ready state for the first end of the lancet handle to insert into to hide the needle tip when the first face faces down to stably rest on the flat surface.

5. The disposable lancet according to claim 4, wherein the block structure is a flat structure having a top surface and a bottom surface, and the top surface of the flat structure is the first face and the bottom surface of the flat structure is the second face.

* * * * *